US00RE42126E

(19) United States
(12) Reissued Patent
Ye et al.

(10) Patent Number: US RE42,126 E
(45) Date of Reissued Patent: *Feb. 8, 2011

(54) DELIVERY SYSTEM FOR ORAL CARE COMPOSITIONS COMPRISING ORGANOSILOXANE RESINS USING A REMOVABLE BACKING STRIP

(75) Inventors: Hai Ye, Brooklyn, NY (US); Christopher David Buckley, Beijing (CN); Jiang Yue, West Chester, OH (US)

(73) Assignee: The Procter & Gamble Company, Cincinnati, OH (US)

( * ) Notice: This patent is subject to a terminal disclaimer.

(21) Appl. No.: 10/927,655

(22) PCT Filed: Jun. 30, 2000

(86) PCT No.: PCT/US00/18188

§ 371 (c)(1), (2), (4) Date: Mar. 20, 2002

(87) PCT Pub. No.: WO01/01958

PCT Pub. Date: Jan. 11, 2001

Related U.S. Patent Documents

Reissue of:
(64) Patent No.: 6,649,147
Issued: Nov. 18, 2003
Appl. No.: 10/019,032
Filed: Mar. 20, 2002

(51) Int. Cl.

| | |
|---|---|
| ***A61K 8/00*** | (2006.01) |
| ***A61K 8/18*** | (2006.01) |
| ***A61K 8/02*** | (2006.01) |
| ***A61K 9/70*** | (2006.01) |
| ***A01N 25/34*** | (2006.01) |
| ***A61F 13/00*** | (2006.01) |
| ***A61L 15/16*** | (2006.01) |

(52) U.S. Cl. ..... 424/49; 424/401; 424/414; 424/443; 424/447; 433/217.1; 433/228.1

(58) Field of Classification Search ..... 424/49, 424/401, 414, 443, 447; 433/217, 228.1
See application file for complete search history.

(56) References Cited

U.S. PATENT DOCUMENTS 2,835,628 A 5/1958 Saffir (Continued)

FOREIGN PATENT DOCUMENTS

AU 601478 B2 9/1990

(Continued)

OTHER PUBLICATIONS

Wikepedia, entry for "Silicone Resin", http://en.wikipedia.org/wiki/Silicone_resin, retrieved Nov. 25, 2006.*

(Continued)

*Primary Examiner*—Frederick Krass
*Assistant Examiner*—Benjamin Packard

(57) ABSTRACT

Disclosed is a delivery system for delivering an oral care substance to the oral cavity, the delivery system comprising: (a) a removable backing strip having sufficient flexibility so as to be readily conformable to an oral surface when the delivery system is placed thereagainst; and (b) an oral care composition applied to the strip of material such that when the delivery system is placed on the oral surface the oral care composition contacts the oral surface, the oral care composition comprising: (i) an organosiloxane resin; (ii) a theology modifier; and (iii) at least one oral care substance; wherein the oral care composition remains on the oral surface after the backing strip is removed. Further disclosed are such delivery systems in which the oral care composition further comprises fluid diorganopolysiloxane-based polymers; such compositions may further comprise carriers for solubilizing the organosiloxane resin and the fluid diorganopolysiloxane-based polymers. Still further disclosed are methods of using the delivery systems.

41 Claims, 3 Drawing Sheets

U.S. PATENT DOCUMENTS

| | | | | | |
|---|---|---|---|---|---|
| 3,070,102 | A | | 12/1962 | MacDonald | |
| 3,096,202 | A | | 7/1963 | De Groot Von Arx | |
| 3,444,858 | A | | 5/1969 | Russell | |
| 3,598,123 | A | | 8/1971 | Zaffaroni | |
| 3,625,215 | A | | 12/1971 | Quisling | |
| 3,640,741 | A | | 2/1972 | Etes | |
| 3,657,413 | A | | 4/1972 | Rosenthal et al. | |
| 3,688,406 | A | | 9/1972 | Porter et al. | |
| 3,754,332 | A | | 8/1973 | Warren, Jr. | |
| 3,784,390 | A | | 1/1974 | Hijiya et al. | |
| 3,844,266 | A | | 10/1974 | Cowen | |
| 3,902,509 | A | | 9/1975 | Tundermann et al. | |
| 3,955,281 | A | | 5/1976 | Weitzman | |
| 3,972,995 | A | | 8/1976 | Tsuk et al. | |
| 3,998,215 | A | | 12/1976 | Anderson et al. | |
| 4,029,757 | A | | 6/1977 | Miodozeniec et al. | |
| 4,029,758 | A | | 6/1977 | Miodozeniec et al. | |
| 4,031,200 | A | | 6/1977 | Reif | |
| 4,032,627 | A | * | 6/1977 | Suchan et al. | 424/54 |
| 4,072,551 | A | | 2/1978 | Dabal et al. | |
| 4,136,145 | A | | 1/1979 | Fuchs et al. | |
| 4,136,162 | A | | 1/1979 | Fuchs et al. | |
| 4,138,314 | A | | 2/1979 | Patil et al. | |
| 4,138,814 | A | | 2/1979 | Weitzman | |
| 4,139,627 | A | | 2/1979 | Lane et al. | |
| 4,182,222 | A | | 1/1980 | Stahl | |
| 4,211,330 | A | | 7/1980 | Strock | |
| 4,251,400 | A | | 2/1981 | Columbus | |
| 4,292,299 | A | | 9/1981 | Suzuki et al. | |
| 4,294,820 | A | | 10/1981 | Keith et al. | |
| 4,307,075 | A | | 12/1981 | Martin | |
| 4,308,250 | A | | 12/1981 | Griffin et al. | |
| 4,324,547 | A | | 4/1982 | Arcan et al. | |
| 4,325,855 | A | | 4/1982 | Dickmann et al. | |
| 4,331,576 | A | | 5/1982 | Colon et al. | |
| 4,335,731 | A | | 6/1982 | Bora, Jr. | |
| 4,363,843 | A | | 12/1982 | Crofts | |
| 4,373,036 | A | | 2/1983 | Chang et al. | |
| 4,376,628 | A | | 3/1983 | Aardse | |
| 4,428,373 | A | | 1/1984 | Seid et al. | |
| 4,431,631 | A | | 2/1984 | Clipper et al. | |
| 4,438,258 | A | | 3/1984 | Graham | |
| 4,442,258 | A | | 4/1984 | Sunakawa et al. | |
| 4,460,562 | A | | 7/1984 | Keith et al. | |
| 4,503,070 | A | | 3/1985 | Eby, III | |
| 4,515,162 | A | | 5/1985 | Yamamoto et al. | |
| 4,517,173 | A | | 5/1985 | Kizawa et al. | |
| 4,518,721 | A | | 5/1985 | Dhabhar et al. | |
| 4,522,805 | A | | 6/1985 | Gordon | |
| 4,522,806 | A | | 6/1985 | Muhlemann et al. | |
| 4,528,180 | A | | 7/1985 | Schaeffer | |
| 4,529,748 | A | | 7/1985 | Wienecke | |
| 4,532,063 | A | | 7/1985 | Gueldenzopf | |
| 4,537,778 | A | | 8/1985 | Clipper et al. | |
| 4,544,354 | A | | 10/1985 | Gores et al. | |
| 4,554,154 | A | | 11/1985 | White | |
| 4,557,692 | A | | 12/1985 | Chorbajian | |
| 4,560,351 | A | | 12/1985 | Osborne | |
| 4,568,536 | A | | 2/1986 | Kronenthal et al. | |
| 4,592,487 | A | | 6/1986 | Simon et al. | |
| 4,592,488 | A | | 6/1986 | Simon et al. | |
| 4,593,053 | A | | 6/1986 | Jevne et al. | |
| 4,623,394 | A | * | 11/1986 | Nakamura et al. | 106/122 |
| 4,650,665 | A | | 3/1987 | Kronenthal et al. | |
| 4,661,070 | A | | 4/1987 | Friedman | |
| 4,687,663 | A | | 8/1987 | Schaeffer | |
| 4,690,996 | A | | 9/1987 | Shih et al. | |
| 4,696,757 | A | | 9/1987 | Blank et al. | |
| 4,712,460 | A | | 12/1987 | Allen et al. | |
| 4,713,239 | A | | 12/1987 | Babaian et al. | |
| 4,713,243 | A | | 12/1987 | Schiraldi et al. | |
| 4,722,761 | A | | 2/1988 | Cartmell et al. | |
| 4,728,291 | A | | 3/1988 | Golub | |
| 4,741,700 | A | | 5/1988 | Barabe | |
| 4,741,941 | A | | 5/1988 | Englebert et al. | |
| 4,755,385 | A | | 7/1988 | Etienne et al. | |
| 4,755,386 | A | | 7/1988 | Hsiao et al. | |
| 4,765,983 | A | | 8/1988 | Takayanagi et al. | |
| 4,770,634 | A | | 9/1988 | Pellico | |
| 4,772,470 | A | | 9/1988 | Inoue et al. | |
| 4,777,046 | A | | 10/1988 | Iwakura et al. | |
| 4,786,253 | A | | 11/1988 | Morais | |
| 4,788,052 | A | | 11/1988 | Ng et al. | |
| 4,797,283 | A | | 1/1989 | Allen et al. | |
| 4,799,888 | A | | 1/1989 | Golub | |
| 4,812,308 | A | | 3/1989 | Winston et al. | |
| 4,837,008 | A | | 6/1989 | Rudy et al. | |
| 4,839,156 | A | | 6/1989 | Ng et al. | |
| 4,839,157 | A | | 6/1989 | Mei-King Ng et al. | |
| 4,842,854 | A | * | 6/1989 | Babaian et al. | 424/78.18 |
| 4,849,213 | A | | 7/1989 | Schaeffer | |
| 4,849,246 | A | | 7/1989 | Schmidt | |
| 4,860,754 | A | | 8/1989 | Sharik et al. | |
| 4,876,092 | A | | 10/1989 | Mizobuchi et al. | |
| 4,891,400 | A | * | 1/1990 | Schwabe et al. | 524/745 |
| 4,895,721 | A | | 1/1990 | Drucker | |
| 4,900,552 | A | | 2/1990 | Sanvordeker et al. | |
| 4,900,554 | A | | 2/1990 | Yanagibashi et al. | |
| 4,902,227 | A | | 2/1990 | Smith | |
| 4,910,247 | A | | 3/1990 | Haldar et al. | |
| 4,915,950 | A | | 4/1990 | Miranda et al. | |
| 4,919,615 | A | | 4/1990 | Croll | |
| 4,925,670 | A | | 5/1990 | Schmidt | |
| 4,927,634 | A | | 5/1990 | Sorrentino et al. | |
| 4,927,636 | A | | 5/1990 | Hijiya et al. | |
| 4,931,282 | A | | 6/1990 | Asmus et al. | |
| 4,948,580 | A | | 8/1990 | Browing | |
| 4,968,251 | A | | 11/1990 | Darnell | |
| 4,971,782 | A | | 11/1990 | Rudy et al. | |
| 4,972,946 | A | | 11/1990 | Whittaker | |
| 4,978,531 | A | | 12/1990 | Yamazaki et al. | |
| 4,980,152 | A | | 12/1990 | Frazier et al. | |
| 4,983,379 | A | | 1/1991 | Schaeffer | |
| 4,983,381 | A | | 1/1991 | Zaragoza | |
| 4,988,500 | A | | 1/1991 | Hunter et al. | |
| 4,990,089 | A | | 2/1991 | Munro | |
| 5,001,170 | A | | 3/1991 | Keegan | |
| 5,024,701 | A | | 6/1991 | Desmarais | |
| 5,047,244 | A | | 9/1991 | Sanvordeker et al. | |
| 5,059,417 | A | | 10/1991 | Williams et al. | |
| 5,064,717 | A | | 11/1991 | Suzuki et al. | |
| 5,076,791 | A | | 12/1991 | Madray, Jr. | |
| 5,084,268 | A | | 1/1992 | Thaier | |
| 5,098,303 | A | | 3/1992 | Fischer | |
| 5,122,365 | A | | 6/1992 | Murayama | |
| 5,158,825 | A | | 10/1992 | Altwirth | |
| 5,160,737 | A | | 11/1992 | Friedman et al. | |
| 5,165,424 | A | * | 11/1992 | Silverman | 128/861 |
| 5,166,233 | A | | 11/1992 | Kuroya et al. | |
| 5,171,564 | A | | 12/1992 | Nathoo et al. | |
| 5,186,938 | A | | 2/1993 | Sablotsky et al. | |
| RE34,196 | E | | 3/1993 | Munroe | |
| 5,192,802 | A | | 3/1993 | Rencher | |
| 5,197,331 | A | * | 3/1993 | Oikawa | 73/504.12 |
| 5,211,559 | A | | 5/1993 | Hart et al. | |
| 5,229,164 | A | | 7/1993 | Pins et al. | |
| 5,234,342 | A | | 8/1993 | Fischer | |
| 5,252,334 | A | | 10/1993 | Chiang et al. | |
| 5,256,402 | A | | 10/1993 | Prencipe et al. | |
| 5,271,940 | A | | 12/1993 | Cleary et al. | |
| 5,288,498 | A | | 2/1994 | Stanley et al. | |

5,290,566 A 3/1994 Schow et al.
5,310,563 A 5/1994 Curtis et al.
5,314,915 A 5/1994 Rencher
5,326,685 A 7/1994 Gaglio et al.
5,330,746 A 7/1994 Friedman et al.
5,332,576 A 7/1994 Mantelle
5,340,314 A 8/1994 Tarvis
5,340,581 A 8/1994 Tseng et al.
5,344,702 A 9/1994 Haubs et al.
5,354,551 A 10/1994 Schmidt
5,356,291 A 10/1994 Darnell
5,376,006 A 12/1994 Fischer
5,380,198 A 1/1995 Suhonen
5,393,528 A 2/1995 Staab
5,401,495 A 3/1995 Murayama
5,401,528 A * 3/1995 Schmidt ..... 427/2.26
5,409,631 A 4/1995 Fischer
5,425,953 A * 6/1995 Sintov et al. ..... 424/404
5,427,770 A * 6/1995 Viccaro et al. ..... 424/54
5,438,076 A * 8/1995 Friedman et al. ..... 514/772.6
5,455,043 A 10/1995 Fischel-Ghodsian
5,462,749 A 10/1995 Rencher
5,472,704 A 12/1995 Santus et al.
5,474,780 A 12/1995 Chang
5,505,933 A 4/1996 Norfleet et al.
5,522,726 A 6/1996 Hodosh
5,529,782 A 6/1996 Staab
5,560,379 A 10/1996 Pieczenik
5,565,190 A 10/1996 Santalucia et al.
5,575,654 A 11/1996 Fontenot
5,575,655 A 11/1996 Darnell
5,579,523 A * 11/1996 Tanaka ..... 710/200
5,593,684 A 1/1997 Baker et al.
5,599,553 A 2/1997 Chung
5,611,687 A 3/1997 Wagner
5,613,942 A * 3/1997 Lucast et al. ..... 602/52
5,620,322 A 4/1997 Lococo
5,620,757 A * 4/1997 Ninomiya et al. ..... 428/34.8
5,626,866 A 5/1997 Ebert et al.
5,629,003 A 5/1997 Horstmann et al.
5,631,000 A 5/1997 Pellico et al.
5,639,445 A 6/1997 Curtis et al.
5,660,178 A 8/1997 Kantner et al.
5,662,758 A 9/1997 Hamilton et al.
5,678,273 A 10/1997 Porcelli
5,700,478 A 12/1997 Biegajski et al.
5,707,235 A 1/1998 Knutson
5,707,736 A 1/1998 Levy et al.
5,713,738 A 2/1998 Yarborough
5,723,132 A 3/1998 Tseng et al.
5,725,843 A 3/1998 Fischer
5,746,598 A 5/1998 Fischer
5,759,037 A 6/1998 Fischer
5,759,038 A 6/1998 Fischer
5,766,011 A 6/1998 Sibner
5,770,105 A 6/1998 Fischer
5,770,182 A 6/1998 Fischer
5,770,219 A 6/1998 Chiang et al.
5,780,045 A 7/1998 McQuinn et al.
5,800,832 A * 9/1998 Tapolsky et al. ..... 424/449
5,819,765 A 10/1998 Mittiga
5,827,591 A 10/1998 Blok et al.
5,846,058 A 12/1998 Fischer
5,851,512 A 12/1998 Fischer
5,851,551 A 12/1998 Tseng et al.
5,855,870 A 1/1999 Fischer
5,856,282 A * 1/1999 Hughes ..... 510/117
5,858,332 A 1/1999 Jensen et al.
5,879,691 A 3/1999 Sagel et al.
5,891,453 A 4/1999 Sagel et al.
5,894,017 A 4/1999 Sagel et al.
5,922,307 A 7/1999 Montgomery
5,948,430 A 9/1999 Zerbe et al.
5,953,885 A 9/1999 Berman et al.
5,968,633 A 10/1999 Hamilton et al.
5,980,249 A 11/1999 Fontenot
5,980,932 A 11/1999 Chiang et al.
5,985,249 A 11/1999 Fischer
5,989,569 A 11/1999 Dirksing et al.
6,008,171 A * 12/1999 Hughes et al. ..... 510/117
6,019,962 A * 2/2000 Rabe et al. ..... 424/64
6,024,891 A * 2/2000 Hughes ..... 252/186.31
6,036,943 A 3/2000 Fischer
6,045,811 A 4/2000 Dirksing et al.
6,071,503 A * 6/2000 Drechsler et al. ..... 424/64
6,072,100 A 6/2000 Mooney et al.
6,074,654 A * 6/2000 Drechsler et al. ..... 424/401
6,083,421 A * 7/2000 Huang et al. ..... 252/186.28
6,090,401 A 7/2000 Gowan, Jr. et al.
6,094,889 A 8/2000 VanLoon et al.
6,096,328 A 8/2000 Sagel et al.
6,123,950 A * 9/2000 Hughes ..... 424/401
6,129,929 A * 10/2000 Wick ..... 424/448
6,136,297 A 10/2000 Sagel et al.
6,139,823 A * 10/2000 Drechsler et al. ..... 424/64
6,159,498 A 12/2000 Tapolsky et al.
6,177,096 B1 1/2001 Zerbe et al.
6,182,420 B1 2/2001 Berman et al.
6,197,331 B1 3/2001 Lerner et al.
6,210,699 B1 4/2001 Acharya et al.
6,231,957 B1 5/2001 Zerbe et al.
6,277,458 B1 8/2001 Dirksing et al.
6,284,264 B1 9/2001 Zerbe et al.
6,306,370 B1 10/2001 Jensen et al.
6,309,625 B1 10/2001 Jensen et al.
6,322,360 B1 11/2001 Burgio
6,331,292 B1 12/2001 Montgomery
6,337,086 B1 * 1/2002 Kanios et al. ..... 424/449
6,340,466 B1 * 1/2002 Drechsler et al. ..... 424/401
6,375,963 B1 4/2002 Repka et al.
6,379,654 B1 4/2002 Gebreselassie et al.
6,406,683 B1 * 6/2002 Drechsler et al. ..... 424/64
6,419,903 B1 7/2002 Xu et al.
6,419,906 B1 7/2002 Xu et al.
6,461,158 B1 10/2002 Sagel et al.
6,488,914 B2 12/2002 Montgomery
6,500,408 B2 12/2002 Chen
6,514,483 B2 2/2003 Xu et al.
6,517,350 B2 2/2003 Diasti et al.
6,537,565 B2 3/2003 Swanbom et al.
6,551,579 B2 4/2003 Sagel et al.
6,552,024 B1 4/2003 Chen et al.
6,582,708 B1 * 6/2003 Sagel et al. ..... 424/401
6,592,887 B2 7/2003 Zerbe et al.
6,596,298 B2 7/2003 Leung et al.
6,669,930 B1 12/2003 Hoic et al.
6,673,361 B1 1/2004 Ogura et al.
6,682,721 B2 1/2004 Kim et al.
6,682,756 B1 1/2004 Horstmann et al.
6,689,344 B2 2/2004 Chang et al.
6,703,040 B2 3/2004 Katsarava et al.
6,709,671 B2 3/2004 Zerbe et al.
6,719,995 B2 4/2004 Rajaiah et al.
6,730,316 B2 5/2004 Chen
6,737,080 B1 5/2004 Schumann
2001/0022964 A1 9/2001 Leung et al.
2002/0081556 A1 6/2002 Tseng et al.
2002/0127190 A1 9/2002 Zerbe et al.
2002/0127254 A1 9/2002 Fotinos et al.
2002/0131990 A1 9/2002 Barkalow et al.
2002/0187181 A1 12/2002 Godbey et al.
2003/0035841 A1 2/2003 Dzija et al.

| | | | |
|---|---|---|---|
| 2003/0049209 | A1 | 3/2003 | Tseng |
| 2003/0054039 | A1 | 3/2003 | Zyck et al. |
| 2003/0099690 | A1 | 5/2003 | Awamura et al. |
| 2003/0152528 | A1 | 8/2003 | Singh et al. |
| 2003/0170308 | A1 | 9/2003 | Cleary et al. |
| 2003/0194382 | A1 | 10/2003 | Chang et al. |
| 2003/0219390 | A1 | 11/2003 | Santarpia, III et al. |
| 2003/0228264 | A1 | 12/2003 | Perna |
| 2004/0022755 | A1 | 2/2004 | Kamar |
| 2004/0043134 | A1 | 3/2004 | Corriveau et al. |
| 2004/0062724 | A1 | 4/2004 | Moro et al. |
| 2004/0086468 | A1 | 5/2004 | Prosise et al. |
| 2004/0091432 | A1 | 5/2004 | Dulin |
| 2004/0096569 | A1 | 5/2004 | Barkalow et al. |
| 2004/0101496 | A1 | 5/2004 | Chen |
| 2004/0105834 | A1 | 6/2004 | Singh et al. |
| 2004/0136927 | A1 | 7/2004 | Kim et al. |
| 2005/0031675 | A1 | 2/2005 | Spence Leung et al. |
| 2005/0048102 | A1 | 3/2005 | Tapolsky et al. |
| 2005/0147658 | A1 | 7/2005 | Tapolsky et al. |

FOREIGN PATENT DOCUMENTS

| | | | |
|---|---|---|---|
| CA | 681997 | | 3/1964 |
| CA | 1209761 | | 8/1986 |
| CA | 2078960 | | 10/1993 |
| CA | 2095445 | | 7/1995 |
| CA | 2000040 | | 10/1995 |
| CA | 2162536 | | 5/1996 |
| CA | 2162812 | | 5/1996 |
| CA | 2162885 | | 5/1996 |
| DE | 1104116 | | 4/1961 |
| DE | 2330869 | | 1/1975 |
| EP | 0 109 269 | A1 | 5/1984 |
| EP | 0 109 269 | B1 | 7/1986 |
| EP | 0 200 508 | | 12/1986 |
| EP | 0 219 762 | | 4/1987 |
| EP | 0 232 006 | A2 | 8/1987 |
| EP | 0 252 459 | | 1/1988 |
| EP | 0 273 069 | A1 | 7/1988 |
| EP | 0 288 420 | A1 | 10/1988 |
| EP | 0 328 317 | A1 | 8/1989 |
| EP | 0 381 194 | | 8/1990 |
| EP | 0 273 069 | B1 | 10/1992 |
| EP | 0 539 751 | A1 | 5/1993 |
| EP | 0 569 797 | A2 | 11/1993 |
| EP | 0 599 435 | A1 | 6/1994 |
| EP | 0 636 378 | A1 | 2/1995 |
| EP | 0 637 446 | A1 | 2/1995 |
| EP | 0 763 358 | | 9/1996 |
| EP | 1 153 594 | A2 | 11/2001 |
| FR | 2637 175 | A1 | 4/1990 |
| GB | 1142325 | | 2/1969 |
| GB | 1240411 | | 7/1971 |
| GB | 2108841 | | 5/1983 |
| GB | 2 115 431 | A | 9/1983 |
| GB | 2 159 052 | A | 11/1985 |
| IE | 42604 | | 9/1980 |
| JP | 57-028102 | | 2/1982 |
| JP | 61280423 | | 12/1986 |
| JP | 6354318 | | 3/1988 |
| JP | 1040423 | | 2/1989 |
| JP | 1-279838 | | 11/1989 |
| JP | 2250826 | | 10/1990 |
| JP | 3198754 | | 8/1991 |
| JP | 3-264522 | | 11/1991 |
| JP | 3-264523 | | 11/1991 |
| JP | 5-124954 | | 5/1993 |
| JP | 5220203 | A2 | 8/1993 |
| JP | 5-236885 | | 9/1993 |
| JP | 7-100186 | | 4/1995 |
| JP | 8183732 | | 7/1996 |
| JP | 08325128 | A2 | 12/1996 |
| JP | 10-17448 | | 1/1998 |
| JP | 10026639 | | 8/1998 |
| JP | 2003137756 | A2 | 5/2003 |
| RU | 2075965 | | 9/1994 |
| WO | WO 91/06270 | | 5/1991 |
| WO | WO 91/06289 | | 5/1991 |
| WO | WO 91/16041 | | 10/1991 |
| WO | WO 98/55079 | * | 12/1998 |
| WO | WO 99/62472 | * | 12/1999 |
| WO | WO 99/66870 | | 12/1999 |
| WO | WO 00/42992 | | 7/2000 |
| WO | WO 01/01958 | A1 | 1/2001 |
| WO | WO 02/02085 | A2 | 1/2002 |
| WO | WO 02/26196 | A1 | 4/2002 |
| WO | WO 02/02085 | A3 | 6/2002 |
| WO | WO 02/43657 | A2 | 6/2002 |
| WO | WO 02/092049 | A2 | 11/2002 |
| WO | WO 03/011259 | A1 | 2/2003 |
| WO | WO 03/043659 | A1 | 5/2003 |

OTHER PUBLICATIONS

3M Dental Products 2000 Product Catalog, 32 pages.

Besner, E., et al., Practical Endodontics, 1994, pp. 7–15, 178–180; Mosby–Year Book, Inc.

S.M. Newman, et al., "Tray–Forming Technique for Dentist– Supervised Home Bleaching", *Quintessence International,* 1995, pp. 447–453, vol. 26, No. 7.

Howard Frysh, BDS, DDS., "Chemistry of Bleaching", *Complete Dental Bleaching,* 1995, pp. 25–32 & 90–97, Quintessence Publishing Co, Inc.

V.B. Haywood, et al., "Nightguard Vital Bleaching", *Quintessence International,* 1989, vol. 20, No. 3, pp. 173–176, 19$^{th}$ International Meeting on Dental Implants and Transplants, Bologna, Italy.

V.B. Haywood, "History, Safety, and Effectiveness of Current Bleaching Techniques and Applications of the Nightguard Vital Bleaching Technique", *Quintessence International,* 1992, vol. 23, No. 7, pp. 471–488.

V.B. Haywood, "Nightguard Vital Bleaching", *Dentistry Today,* 1997, pp. 86–91.

"Tooth Bleaching, Home–Use Products", *Clinical Research Associates Newsletter,* 1989, vol. 3, Issue 12.

Ralph H. Leonard Jr., et al, "Risk factors for developing tooth sensitivity and gingival irritation associated with nightguard vital bleaching", *Esthetic Dentristy,* 1997, vol. 28, No. 8, pp. 527–534.

Van B. Haywood, et al, "Nightguard vital bleaching, how safe is it?", *Esthetic Dentistry,* 1991, vol. 22, No. 7, pp. 515–523.

Van B. Haywood, "History, safety and effectiveness of current bleaching techniques and applications of the nightguard vital bleaching technique", *Esthetic Dentistry,* 1992, vol. 23, No. 7, pp. 471–488.

Van B. Haywood, "Bleaching of vital and notvital teeth", *Periodontology and Restorative Dentistry,* 1992, pp. 142–149.

Van B. Haywood, "Nightguard vital bleaching, a history and products update: Part 1", *Esthetic Dentistry Update,* 1991, vol. 2, No. 4, pp. 63–66.

Van B. Haywood, "Nightguard vital bleaching, a history and products update: Part 2", *Esthetic Dentistry Update,* 1991, vol. 2, No. 5, pp. 82–85.

Claudia Paula Drew, "Teeth Bleaching . . . a Vital technique for you to know", Sep./Oct. 1988, pp. 23–25.

Van Benjamin Haywood, "Overview and Status of Mouthguard Bleaching" *Journal of Esthetic Dentistry,* 1991, vol. 3, No. 5, pp. 157–161.
Van B. Haywood, "Nightguard vital bleaching: current information and research", *Esthetic Dentistry Update,* 1990, vol. 1, No. 2, pp. 20–25.
Carolyn F. G. Wilson, et al, "Color change following vital bleaching of tetracycline–stained teeth" *Pediatric Dentistry,* 1985, vol. 7, No. 3, pp. 205–208.
"Tooth Bleaching, Home–Use Products", *Clinical Research Associates Newsletter,* 1989, pp. 1–4.
Sue Ellen Richardson, "Home bleaching: effectiveness, history, technique, bleaches, cost and safety" *The Journal of the Greater Houston Dental Society,* 1989, pp. 22–26.
Van B. Haywood, "The food and drug administration and its influence on home bleaching", *ADA,* 1993, pp. 12–18.
Van B. Haywood, "Efficacy of foam liner in 10% carbamide peroxide bleaching technique", *Esthetic Dentistry,* 1993, vol. 24, No. 9, pp. 663–666.
Christopher J. Woolverton, "Toxicity of two carbamide peroxide products used in nightguard vital bleaching", *American Journal of Dentistry,* 1993, vol. 6, No. 6, pp. 310–314.
Van B. Haywood, "Response of normal and tetracycline–stained teeth with pulp–size variation to nightguard vital bleaching", *Journal of Esthetic Dentistry,* 1994, vol. 6, No. 3, pp. 109–114.
Ralph H. Leonard, et al, "Salivary pH changes during 10% carbamide peroxide bleaching" *Dental Research,* 1994, vol. 25, No. 8, pp. 547–550.
Ralph H. Leonard, et al, "Change in pH of plaque and 10% carbamide peroxide solution during nightguard vial bleaching treatment" *Esthetic Dentistry,* 1994, vol. 25, No. 12, pp. 819–823.
Van B. Haywood, "Historical development of whiteners: clinical safety and efficacy", *Aesthetics,* 1997, pp. 98–104.
Van B. Haywood, "Considerations and variations of dentist–prescribed,home–applied vital tooth–bleaching techniques", *Compend Contin Educ Dent,* 1994, Suppl.No. 17, pp. s616–s621.
Van B. Haywood, "Effectiness, side effects and long–term status of nightguard vital bleaching", *JADA,* 1994, vol. 125, pp. 1219–1226.
James W. Curtis, et al, "Assessing the effects of 10 percent carbamide peroxide on oral soft tissues", JADA, 1996, vol. 127, pp. 1218–1223.
Fonda G. Robinson, et al, "Effect of 10 percent carbamide peroxide on color of provisional restoration materials", *JADA,* 1997, vol. 128, pp. 727–731.
Van B. Haywood, "Commonly asked questions about nightguard vital bleaching", *IDA Journal,* 1993, pp. 28–33.
Van B. Haywood, "Nightguard vital bleaching: current concepts and research", *JADA,* 1997, vol. 128, pp. 19s–25s.
Van B. Haywood, "Commonly asked question about nightguard vital bleaching", *The Dental Assistant,* Mar./Apr. 1996, pp. 6–12.
M.S. McCracken, "Demineralization effects of 10 percent carbamide peroxide", *Journal of Dentistry,* 1996, vol. 24, No. 6, pp. 395–398.
Messing, J.J., et al., *Color Atlas of Endodontics,* 1988, pp. 106–107, 135–140, 173–175, 257–259; The C.V. Mosby Company, Ltd.
Van B. Haywood, "Efficacy of six months of nightguard vital bleaching of tetracycline–stained teeth", *Journal of Esthetic Dentistry,* 1997, vol. 9, No. 1, pp. 13–19.
Van B. Haywood, "Achieving, maintaining and recovering successful tooth bleaching", *Journal of Esthetic Dentistry,* 1996, vol. 8, No. 1, pp. 31–38.
Carl M. Russell, et al, "Dentist–supervised home bleaching with ten percent carbamide peroxide gel: a six month study", *Journal of Esthetic Dentistry,* 1996, vol. 8, No. 4, pp. 177–182.
Van B. Haywood, "Historical development of whiteners: clinical safety and efficacy", *Aesthetics,* 1997, April update, pp. 98–104.
Office Action from the United States Patent & Trademark Office, dated Sep. 5, 2003, issued on U.S. Appl. No. 09/864,686, filed May 24, 2001, assignee—The Procter & Gamble Company, now abandoned.
Office Action from the United States Patent & Trademark Office, dated May 28, 2003, issued on U.S. Appl. No. 09/864,686, filed May 24, 2001, assignee—The Procter & Gamble Company, now abandoned.

* cited by examiner

DELIVERY SYSTEM FOR ORAL CARE COMPOSITIONS COMPRISING ORGANOSILOXANE RESINS USING A REMOVABLE BACKING STRIP

Matter enclosed in heavy brackets [ ] appears in the original patent but forms no part of this reissue specification; matter printed in italics indicates the additions made by reissue.

*CROSS REFERENCE TO RELATED APPLICATIONS*

*This application is a reissue of application Ser. No. 10/019,032, filed Mar. 20, 2002, now U.S. Pat. No. 6,649,147 which was the National Stage of International Application No. PCT/US00/18188 filed Jun. 30, 2000 and which was a continuation-in-part of International Application No. PCT/US/00/15890 filed Jun. 9, 2000; a continuation-in-part of International Application No. PCT/US00/15891 filed Jun. 9, 2000; a continuation-in-part of International Application No. PCT/US99/15130 filed Jul. 2, 1999; and a continuation-in-part of International Application No. PCT/US99/15131 filed Jul. 2, 1999.*

FIELD

The present invention relates to a delivery system for applying and delivering an oral care substance or composition to oral surfaces including the tooth enamel. The composition forms a film on the surface to which it has been applied and provides sustained release of the oral care substance from the film for prolonged therapeutic, prophylactic, and/or cosmetic benefits. More specifically, the present invention relates to systems comprising a removable backing strip to facilitate the application of compositions comprising organosiloxane resins for delivering oral care substances to the tooth enamel. In addition, it is believed that the compositions herein may further provide sustained release benefits to other oral surfaces, such as the gingival and mucosal tissues, as well as to the surfaces of the teeth.

BACKGROUND

Oral care products by which various oral care substances or actives can be delivered to the soft and hard tissues of the oral cavity have previously been known. Examples of such oral care products include, for example, brushing aids such as dentifrice products for delivery of anti-caries actives such as fluoride or other actives for the reduction of the bacteria that lead to the formation of plaque, and mouthwashes containing breath freshening actives and/or anti-bacterial actives. In addition, bleaching agents such as peroxide that can be applied directly to the surfaces of the teeth, i.e., to the tooth enamel, have been developed.

However, it has been found that such conventional product forms typically do not provide substantivity sufficient to maintain actives on the hard and soft oral tissues for a period of time sufficient to enhance or prolong the therapeutic, prophylactic, and/or cosmetic benefits provided by the actives. Neither have such conventional product forms been able to provide sustained delivery of oral care actives, without periodic reapplication at relatively short time intervals, or without a special delivery device or containment means such as a mouthpiece.

One such system is disclosed in International Publication No. [WO 98/55709] *WO 98/55079*, "A Delivery System for an Oral Care Substance Using a Strip of Material Having a Low Flexural Stiffness," published on Dec. 10, 1998. This system involves the combination of an oral care substance that directly contacts the oral cavity surfaces, and a flexible strip of material that is worn over the oral care substance, to protect the substance from erosion and from contact with other oral surfaces and, or saliva. In this system, the strip is worn in order to hold the composition in place for a sufficient amount of time to allow the active to act upon the oral surface.

Other attempts have previously been made to enhance the substantivity of whitening bleaches, bactericides, and other active components of oral care products. See, e.g., U.S. Pat. No. 5,425,953 to Sintov el al. on Jun. 20, 1995, in which a film forming, water-soluble cellulosic polymer is used to deliver a bleaching agent to the teeth; U.S. Pat. No. 5,438,076 to Friedman et al., in which liquid methacrylate acid copolymer compositions are used to deliver a bacteriocidal pharmacological agent; and International Patent Appln. No. PCT/CN97/00 to Huang, published on Jul. 24, 1997, disclosing a film-coating composition comprising cellulose and polyvinyl acetal, coumarone-indene resin, or shellac as a film former to deliver bleaches to the tooth enamel.

However, the above systems are water-soluble, i.e., they are readily dissolved by saliva, generally within about 1–3 hours after application. Therefore, their degree of durability is low, and they cannot provide long-term delivery of the active ingredient that is present in the composition. In addition, their water-soluble nature precludes them from being used with oral care actives that would be unstable in water-based films. Sodium percarbonate is one example of such an active; it would be unstable in the high pH environment of an aqueous-based film.

In order to provide an applied composition with a relatively higher degree of durability, the use of protective coatings that are applied to the teeth has been described. See, U.S. Pat. No. 5,401,528, to Schmidt on Mar. 18, 1995, in which organically modified silicic acid polycondensates are deposited on the teeth, then polymerized in-situ by curing, to coat the teeth in order to protect them from plaque deposits. This system is not a true delivery system by which an active ingredient is released over time; instead, it provides a barrier by which the deleterious effect of plaque-causing bacteria may be diminished.

Although such a barrier coating may offer a benefit in terms of enhanced durability, it requires the use of special equipment and complex application; thus, it cannot be performed at home and cannot be used for self-treatment.

Therefore, it can be seen that none of these previous developments can offer the combination of both long-term delivery of an oral care substance or active ingredient and the convenience of easy application, discreet self-treatment, and home use. Based on the foregoing, there is a need for a convenient delivery system for various oral care substances which is easy to apply and in which the substantivity of the active ingredients is enhanced. None of the existing art provides all of the advantages and benefits of the present invention.

SUMMARY

The present invention is directed to a delivery system for delivering an oral care substance to the oral cavity, the delivery system comprising: (a) a removable backing strip having sufficient flexibility so as to be readily conformable to an oral surface when the delivery system is placed thereagainst; and (b) an oral care composition applied to the strip of material such that when the delivery system is placed on the oral surface the oral care composition contacts the oral surface, the oral care composition comprising: (i) an organosiloxane resin; (ii) a rheology modifier; and (iii) at least one oral care substance; wherein the oral care composition remains on the oral surface after the backing strip is removed.

The present invention is also directed to such systems in which the oral care composition further comprises fluid diorganopblysiloxane-based polymers. Such compositions may further comprise carriers for solubilizing the organosiloxane resin and the fluid diorganopolysiloxane-based polymers.

The present invention is still further directed to methods of using the delivery systems herein.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the present invention, it is believed that the present invention will be better understood from the following description of preferred embodiments, taken in conjunction with the accompanying drawings, in which like reference numerals identify identical elements and wherein:

DETAILED DESCRIPTION

All percentages and ratios used hereinafter are by weight of total composition, unless otherwise indicated.

All measurements referred to herein are made at 25° C. unless otherwise specified.

The abbreviation "cm", as used herein, means centimeter. The abbreviation "mm" as used herein, means millimeter.

All percentages, ratios, and levels of ingredients referred to herein are based on the actual amount of the ingredient, and do not include solvents, fillers, or other materials with which the ingredient may be combined as a commercially available product, unless otherwise indicated.

All publications, patent applications, and issued patents mentioned herein are hereby incorporated in their entirety by reference. Citation of any reference is not an admission regarding any determination as to its availability as prior art to the claimed invention.

Herein, "comprising" means that other steps and other components which do not affect the end result can be added. This term encompasses the terms "consisting of" and "consisting essentially of."

Figure 1:
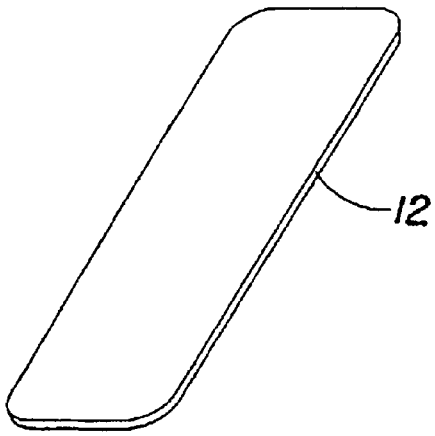
FIG. 1 is a perspective view of a substantially flat backing strip of material.
Figure 2:
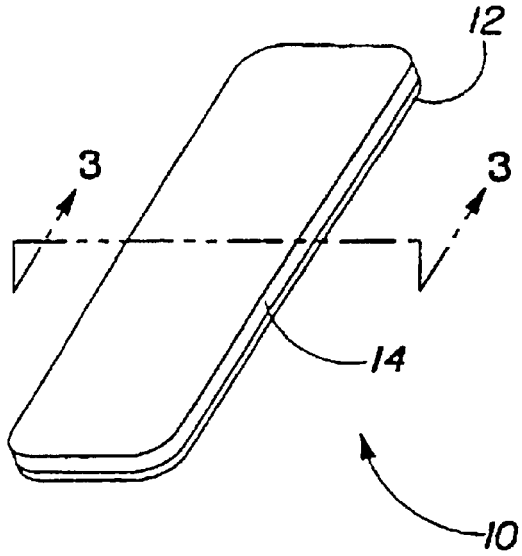
FIG. 2 is a perspective view of an embodiment of the present invention, disclosing the flat backing strip of FIG. 1 coated with an oral care substance for treating teeth and/or gums.

Referring now to the drawings, and more particularly to FIGS. 1 and 2, there is shown a first preferred embodiment of the present invention, generally indicated as 10, representing a delivery system for applying and delivering an oral care composition to an oral surface. Delivery system 10 has a backing strip of material 12, which is initially substantially flat.

Figure 3:
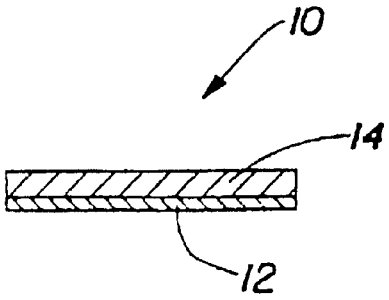
FIG. 3 is a cross-sectional view thereof, taken along section line 3—3 of FIG. 2, disclosing an example of the flat backing strip having a thickness less than that of the substance coated thereon.

Applied or coated onto the backing strip 12 is an oral care composition 14, as described herein. Preferably, the oral care composition 14 is homogeneous, uniformly and continuously coated onto the backing strip 12, as shown in FIG. 3. However, oral care composition 14 may alternatively be a laminate or separated layers of components, an amorphous mixture of components, separate stripes or spots or other patterns of different components, or a combination of these structures including a continuous coating of oral care composition 14 along a longitudinal axis of a portion of the backing strip 12.

Figure 4:
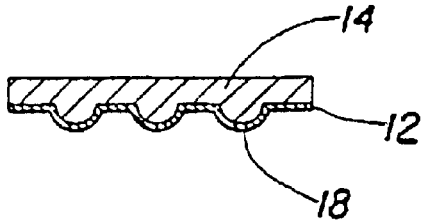
FIG. 4 is a cross-sectional view showing an alternative embodiment of the present invention, showing shallow pockets in the backing strip, which act as reservoirs for additional oral care substance coated on the strip.

As shown in FIG. 4, an alternative embodiment, a backing strip 12 may have shallow pockets 18 formed therein. When oral care composition 14 is coated on a composition-coated side of backing strip 12, additional oral care composition 14 fills shallow pockets 18 to provide reservoirs of additional oral care composition 14.

Figure 5:
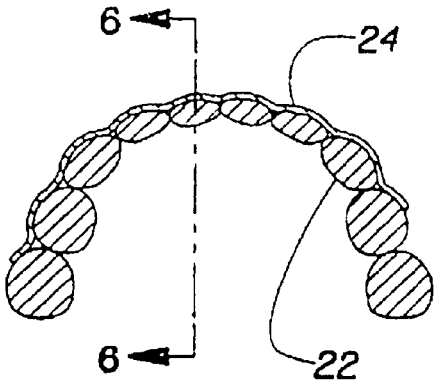
FIG. 5 is a cross-sectional plan view thereof, showing an alternative embodiment for applying oral care substances for treating teeth having the backing strip of the present invention conforming to the teeth and allowing application across typical dentition surfaces.
Figure 6:
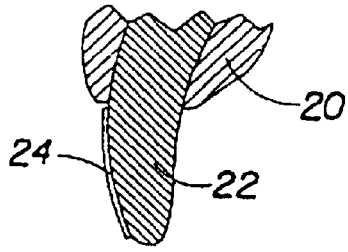
FIG. 6 is a cross-sectional elevation view of a tooth, taken along section line 6—6 of FIG. 5, disclosing the backing strip with oral care active of the present invention conforming to the tooth profile during application.

FIGS. 5 and 6 show a delivery system 24 of the present invention conformed to a surface of a tooth and plurality of adjacent teeth during the application of the delivery system herein. Embedded in adjacent soft tissue 20 are a plurality of adjacent teeth 22. Adjacent soft tissue is herein defined as soft tissue surfaces surrounding the tooth structure including: papilla, marginal gingiva, gingival sulculus, inter dental gingiva, gingival gum structure on lingual and buccal surfaces up to and including muco-ginival junction and the pallet.

In both FIGS. 5 and 6, delivery system 24 represents a backing strip 12 and an oral care composition 14, with oral care composition 14 on the side of the backing strip 12 the is facing tooth 22. Oral care composition 14 may be pre-applied to the backing strip 12, or may be applied to the backing strip 12 by the delivery system user. In either case, the backing strip 12 has a thickness and flexural stiffness which enable it to conform to the contoured surfaces of tooth 22 and to adjacent soft tissue 20 during application of the oral care composition 14. The backing strip has sufficient flexibility to form to the contours of the oral surface, in this figure the surface being a plurality of adjacent teeth. The backing strip is also readily conformable to tooth surfaces and to the interstitial tooth spaces without permanent deformation during application.

Figure 7:
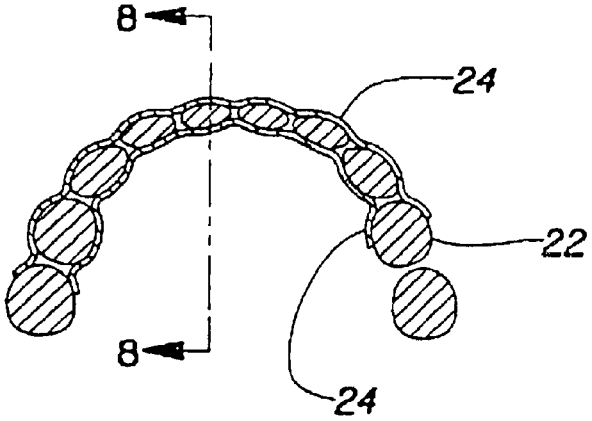
FIG. 7 is a cross-sectional plan view, similar to FIG. 5, showing a backing strip of the present invention conforming to the teeth and the adjoining soft tissue during application.
Figure 8:
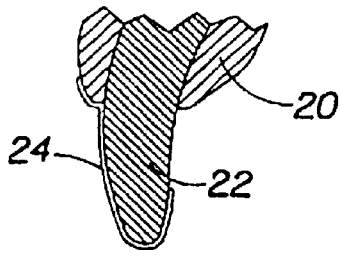
FIG. 8 is a cross-sectional elevation view, taken along section line 8—8 of FIG. 7, showing a backing strip of the present invention conforming to both the tooth and the adjoining soft tissue during application.

FIGS. 7 and 8 show a delivery system 24 of the present invention applied to both front and rear surfaces of a plurality of adjacent teeth 22 as well as to adjacent soft tissue 20, during application of the oral care composition. Delivery system 24 represents a backing strip 12 and an oral care composition 14, with oral care composition 14 on the side of backing strip 12 that is facing tooth 22.

Figure 9:
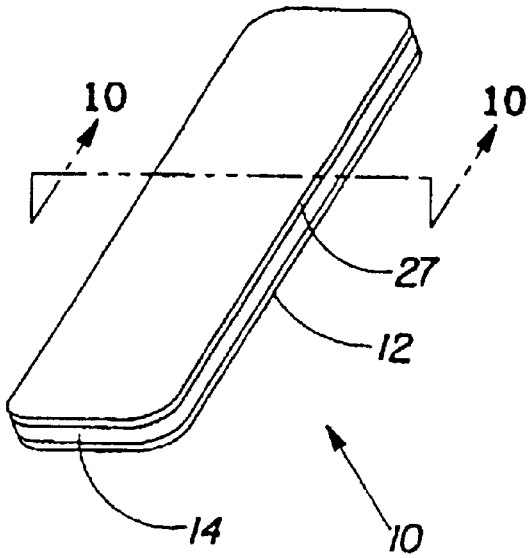
FIG. 9 is a perspective view of an alternative embodiment of the present invention, disclosing the flat backing strip coated with an oral care substance of FIG. 2 for treating teeth and adjoining soft tissue having a release liner.
Figure 10:
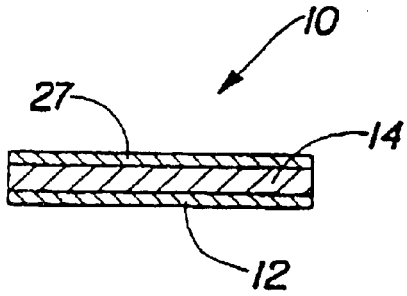
FIG. 10 is a cross-sectional view of an alternative embodiment of the present invention, taken along section line 10—10 of FIG. 9, showing a release liner attached to the backing strip by the oral care substance on the strip of material.

FIGS. 9 and 10 show an optional release liner 27. Release liner 27 is attached to the backing 12 by oral care composition 14. Oral care composition 14 is on the side of the backing strip 12 that is facing the release liner 27. This side is applied to the tooth and gum surfaces once the release liner 27 is removed.

Figure 11:
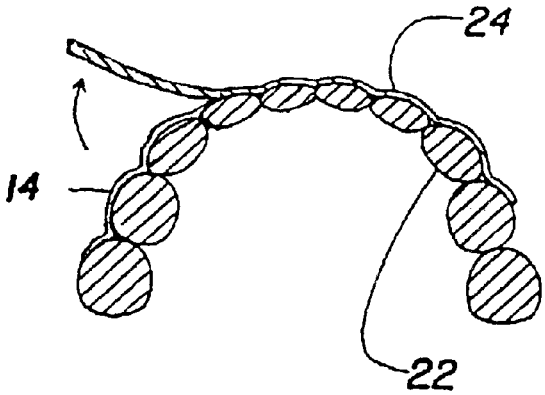
FIG. 11 shows an example of applying the delivery system of the present invention onto the teeth by peeling the backing strip away from the teeth.

FIG. 11 shows an example of applying the delivery system of the present invention onto teeth. The oral care substances will be left on teeth surface after the backing strip is peeled off. Another example of applying the delivery system (not shown) is to allow the backing strip to dissolve in-situ. In such an embodiment, there is no need to peel the backing strip away from the oral surfaces.

Backing Strip of Material

The backing strip of material serves to carry the oral care compositions herein, and facilitates the application of the oral compositions to the oral surfaces. In preferred embodiments of the present invention, the backing strip is removable, i.e., it need not be worn in the oral cavity for the duration of the time that the oral care composition is present in the oral cavity. As used herein, the term "removable" is intended to include manual removal of the backing strip, e.g., by peeling, as well as removal of the backing strip as a result of in-situ dissolution in the oral cavity, i.e., that occurs without the need for manual peeling.

The backing strip of material may comprise polymers, natural and synthetic woven materials, non-woven material, foil, paper, rubber, and combinations thereof. The backing strip may be a single layer of material or a laminate comprised of more than one layer. Regardless of the number of layers, the backing strip is either substantially water soluble (dissolves in-situ) or substantially water insoluble.

In the case of a substantially water insoluble backing strip, the strip may be removed by peeling immediately after application, see FIG. 11, leaving the active materials adhering to the teeth and/or other oral surfaces, or removed after some time interval. Preferably, the material is any type of polymer or combination of polymers that meet the required flexural rigidity and is compatible with oral care substances. Suitable polymers include, but are not limited to, polyethylene, ethylvinylacetate, polyesters, ethylvinyl alcohol, pullulan film, combinations thereof. Examples of polyesters include Mylar® and fluoroplastics such as Teflon®, both manufactured by DuPont. The preferable material is polyethylene. The backing strip is generally less than about 1 mm thick, preferably less than about 0.05 mm thick, and more preferably from about 0.001 to about 0.03 mm thick. A polyethylene backing strip is preferably less than about 0.1 mm thick and more preferably from about 0.005 to about 0.02 mm thick.

The backing strip may also be comprised of a substantially water and/or saliva soluble material such as agar film, starch paper, rice paper, natural gum, pullulan paper, or mixtures thereof. Such embodiments are very convenient for consumer use as they do not require the step of peeling the backing strip away. They may also provide added safety during overnight use, because there is no chance of accidentally swallowing a backing strip that becomes loose during sleeping.

The shape of the backing strip is any shape and size that covers the desired oral surface. The width of the backing strip will also depend upon the oral surface area to be covered. In one example, the width of the strip is from about 0.5 cm to about 4 cm and preferably from about 1 cm to about 2 cm.

The backing strip may contain shallow pockets. When the oral care substance is coated on a such a backing strip, additional oral care substance fills shallow pockets to provide reservoirs of additional oral care substance. Additionally, the shallow pockets help to provide texture to the delivery system. The film will preferably have an array of shallow pockets. Generally, the shallow pockets are approximately 0.4 mm across and 0.1 mm deep. When shallow pockets are included in the backing strip and oral care substances are applied to it in various thicknesses, the overall thickness of the delivery system is generally less than about 1 mm. Preferably, the overall thickness is less than about 0.5 mm.

Oral Care Compositions

The amount of oral care composition applied to the strip of material or oral surface depends upon the size and capacity of the piece of material, concentration of the active, and the desired benefit sought. Generally, less than about 1 gram of oral care substance is required. Preferably, from about 0.05 grams to about 0.5 grams and more preferably from about 0.1 gram to about 0.4 grams of the oral care substance is used. The amount of oral care substance per square cm of material is less than about 0.2 grams/cm$^2$, preferably from about 0.005 to about 0.1 grams/cm$^2$, and more preferably from about 0.01 grams/cm$^2$ to about 0.04 grams/cm$^2$.

The oral care composition of the present invention can be in the form of a viscous liquid, paste, gel, solution, or other suitable form that can provide sufficient adhesion. Preferably, the oral care composition is in the form of an adhesive film. The oral care substance will have a viscosity of from about 200 to about 1,000,000 cps at low shear rates (less than one 1/seconds). Preferably, the viscosity is from about 100,000 to about 800,000 cps and more preferably from about 400,000 to about 600,000 cps.

One preferred embodiment of the oral composition herein is comprised of an organosiloxane resin; a rheology modifier; and at least one oral care substance.

Another preferred embodiment of the composition is comprised of an organosiloxane resin; a fluid diorganopolysiloxane-based polymer; a rheology modifier; and at least one oral care substance. Another preferred embodiment of such an oral care composition further comprises a carrier capable of solubilizing the organosiloxane resin and the fluid diorganopolysiloxane-based polymer. These components are described in greater detail below.

Organosiloxane Resins

Silicone resins are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0.

Silicone materials and silicone resins in particular can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO)_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Note that a small amount, up to about 5% of silanol or alkoxy functionality may also be present in the resin structure as a result of processing.

Primes of the unit symbols, e.g., M', D', T', and Q', denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The organosiloxane resins are solid at about 25° C. and the average molecular weight of the resins is from about 1,000 to about 10,000. The resins are soluble in organic solvents such as toluene, xylene, isoparaffins, and cyclosiloxanes or the volatile carrier described below, indicating that the resin is not sufficiently crosslinked such that the resin is insoluble in the volatile carrier.

The silicone resins preferred for use herein are MQ, MT, MTQ, and MDTQ resins; such MQ resins are disclosed in U.S. Pat. No. 5,330,747, Krzysik, issued Jul. 19, 1994. Thus, the preferred silicone substituent is methyl. Especially preferred are MQ resins wherein the M:Q ratio is from about 0.5:1.0 to about 1.5:1.0. Organosiloxane resins such as these are commercially available, for example, Wacker 803 and 804 available from Wacker Silicones Corporation of Adrian, Mich., US, and G.E. 1170-002 from the General Electric Company.

The level of the resin that is used in the compositions is dependent on its degree of solubility in the formulation, particularly in the solvents used. Generally, the range of resin used in the present invention is from about 5% to about 70%, preferably from about 15% to about 45%, and even more preferably from about 20% to about 40%.

Fluid Diorcanopolysiloxane-based Polymers

In addition to the organosiloxane resins disclosed above, the compositions of the present invention may further comprise a fluid diorganopolysiloxane-based polymer to be combined with the organosiloxane resins. Said fluid diorganopolysiloxane-based polymers useful in the present invention span a large range of viscosities; from about 10 to about 10,000,000 centistokes (cSt) at 25° C. Some diorganopolysiloxane polymers useful in this invention exhibit viscosities greater than 10,000,000 centistokes (cSt) at 25° C. and therefore are characterized by manufacturer specific penetration testing. Examples of this characterization are GE silicone materials SE 30 and SE 63 with penetration specifications of 500–1500 and 250–600 (tenths of a millimeter) respectively.

Among the fluid diorganopolysiloxane-based polymers of the present invention are diorganopolysiloxane polymers comprising repeating units, where said units correspond to the formula $(R_2SiO)_n$, where R is a monovalent hydrocarbon radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof. The fluid diorganopoylsiloxane polymers employed in the present invention may contain one or more of these hydrocarbon radicals as substituents on the siloxane polymer backbone. The fluid diorganopolysiloxane polymers may be terminated by triorganosilyl groups of the formula $(R'_3Si)$ where R' is a radical selected from the group consisting of monovalent hydrocarbons containing from 1–6 carbon atoms, hydroxyl groups, alkoxyl groups and mixtures thereof. The fluid diorganopolysiloxane polymer must be compatible in solution with the organosiloxane resin and the volatile carrier. The term "compatible" refers to the formation of a single phase solution when the fluid diorganopolysiloxane polymer, the organosiloxane resin and the volatile carrier are mixed together in ratios required for a specific formulation. For example, the lower viscosity fluid diorganopolysiloxane polymers (viscosity of about 10 to 100cSt.) are particularly useful when using ethanol as the principal volatile carrier. For higher viscosity polymers, e.g., poly (dimethylsiloxane), herein referred to as PDMS or silicone gum, having a viscosity of at least 100,000 cSt, volatile carriers other than ethanol are preferred.

Silicone gum corresponds to the formula:

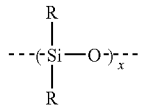

where R is a methyl group.

Fluid diorganopolysiloxane polymers such as these are commercially available, for example, SE 30 silicone gum and SF96 silicone fluid available from the General Electric Company. Similar materials can also be obtained from Dow Coming and from Wacker Silicones.

Another fluid diorganosiloxane-based polymer preferred for use in the present invention is a dimethicone copolyol to modify film forming characteristics as desired. The dimethicone copolyol can be further characterized as polyalkylene oxide modified polydimethysiloxanes, such as manufactured by the Witco Corporation under the trade name Silwet. Similar materials can be obtained from Dow Coming, Wacker Silicones and Goldschmidt Chemical Corporation as well as other silicone manufacturers.

In preferred embodiments of the present invention, the ratio of organosiloxane resin to fluid diorganopolysiloxane polymer is preferably from about 10:1 to about 1:10, more preferably from about 2:1 to about 8:1, and still more preferably from about 4:1 to 6:1.

Rheology Modifiers

The compositions further comprise a rheology modifier which inhibits settling and separation of components or controls settling in a manner which facilitates re-dispersion and may control rheological flow properties for strip making. Suitable rheology modifiers herein include organo modified clays, silicas, polyethylene, and mixtures thereof. The preferred organophilic clays comprise quatemium-18 hectorite or Stearalkonium hectorite, such as Bentone 27 and 38™ from Rheox, organoclay dispersion such as Bentone ISD gel™; or bentonite organo modified clays such as Bentone 34 ™ from Rheox or the Claytone Series™ from Southern Clay Products; and mixtures thereof. The preferred silicas may be fumed silica such as the Aerosil™ series from Degussa or the Cab-o-sil™ series from Cabot Corporation, silica gels such as the Sylodent ™ or Sylox™ series from W. R. Grace & Co. or precipitated silica such as Zeothix 265 from J. M. Huber Corporation.

The rheology modifier is preferably present in the composition at a level of from about 0.1% to about 30%, preferably from about 0.5% to about 10%, and even more preferably about 1% to about 3% of the composition.

Carriers

The oral care compositions that comprise a fluid diorganosiloxane-based polymer may further comprise a carrier. The carrier may be used to solubilize the organosiloxane resin and the fluid diorganosiloxane-based polymer. If present, the carrier is preferably comprised of a volatile component and a non-volatile component. During preparation of a delivery system in which the oral care composition comprises such a carrier, after the composition has been cast onto the backing strip, the volatile component will volatize and the non-volatile component will remain in the composition to provide softness and flexiblity to the backing strip.

The carrier comprises from about 0% to about 90%, preferably from about 0% to about 80%, and more preferably from about 0% to about 70%, of the composition. The carrier of the present invention is selected from the group consisting of hydrocarbon oils, volatile silicones, non-hydrocarbon solvents, and mixtures thereof.

Hydrocarbon oils useful in the present invention include those having boiling points in the range of 60–260° C., more preferably hydrocarbon oils having from about $C_8$ to about $C_{20}$ chain lengths, most preferably $C_8$ to $C_{20}$ isoparaffins. Of these isoparaffins most preferred are selected from the group consisting of isododecane, isohexadecane, isoeocosane, 2,2,4-trimethylpentane, 2,3-dimethylhexane and mixtures thereof. Most preferred is isododecane, available as, for example, Pernethyl 99A from Permethyl Corporation corresponding to the formula:

$$CH_3(CH_2)_{10}CH_3$$

Preferred volatile silicone fluids include cyclomethicones having 3, 4 and 5 membered ring structures corresponding to the formula:

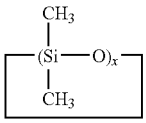

where X is from about 3 to about 6. Such volatile silicones include 244 Fluid, 344 Fluid and 245 Fluid, and 345 Fluid all from Dow Corning Corporation.

The general classes of non-hydrocarbon solvents useful herein include esters, ketones, alcohols, fluorocarbons and fluorocarbon ethers having boiling points in the range of 60 to 200° C. Non-hydrocarbon solvents or mixtures thereof particularly useful include those that are capable of-solubilizing the resin and/or the diorganopolysiloxane-based polymer. Such solvents include but are not limited to ethanol, acetone, butanone, ethyl acetate, propyl acetate, amyl acetate, ethyl butyrate, methyl nonafluoroisobutyl ether, methyl nonafluorobutyl ether, and mixtures thereof. These non-hydrocarbon solvents are readily available such as ethyl acetate and methyl ethyl ketone, both supplied by J. T. Baker of Phillispburg, N.J, and HFE (a mixture of methyl nonafluoroisobutyl ether and methyl nonafluorobutyl ether), supplied by the 3M Company.

Oral Care Substances

The oral care substance preferably contains an active at a level where upon directed use, the benefit sought by the wearer is promoted without detriment to the oral surface to which it is applied. Examples of the oral conditions these actives address include, but, are not limited to, appearance and structural changes to teeth, whitening, stain bleaching, stain removal, plaque removal, tartar removal, cavity prevention and treatment, inflamed and/or bleeding gums, mucosal wounds, lesions, ulcers, aphthous ulcers, cold sores, tooth abscesses, and the elimination of mouth malodor resulting from the conditions above and other causes such as microbial proliferation.

Suitable oral care substances include any material that is generally considered safe for use in the oral cavity and that provides changes to the overall appearance and/or health of the oral cavity. The level of oral care substance in the compositions of the present invention is generally, unless specifically noted, from about 0.01% to about 50%, preferably from about 0.1% to about 20%, more preferably from about 0.5% to about 10%, and even more preferably from about 1% to about 7%, by weight of the composition.

Oral care compositions or substances of the present invention may include many of the actives previously disclosed in the art. The following is a non-limiting list of oral care actives that may be used in the present invention.

1. Teeth Whitening Actives

Teeth whitening actives may be included in the oral care substance of the present invention. The actives suitable for whitening are selected from the group consisting of the peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. The preferred chlorite is sodium chlorite. A preferred percarbonate is sodium percarbonate. Preferred persulfates are oxones.

2. Anti-tartar Agents

Anti-tartar agents known for use in dental care products include phosphates. Phosphates include pyrophosphates, polyphosphates, polyphosphonates and mixtures thereof. Pyrophosphates are among the best known for use in dental care products. Pyrophosphate and polyphosphate ions are delivered to the teeth derive from pyrophosphate polyphosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. While any of the above mentioned pyrophosphate salts may be used, tetrasodium pyrophosphate salt is preferred. Sodium polyphosphate and triethanolamine polyphosphates, for example, are preferred.

The pyrophosphate salts are described in more detail in Kirk & Othmer, Encyclopedia of Chemical Technology, Third Edition, Volume 17, Wiley-Interscience Publishers (1982). Additional anticalculus agents include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Pat. No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al.; as well as, e.g., polyamino propoane sulfonic acid (AMPS), zinc citrate trihydrate, polyphosphates (e.g., tnpolyphosphate; hexametaphosphate), diphosphonates (e.g., EHDP; AHP), polypeptides (such as polyaspartic and polyglutamic acids), and mixtures thereof.

3. Fluoride Ion Source

Fluoride ion sources are well known for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972. Preferred fluoride ion sources for use herein include sodium fluoride, potassium fluoride and ammonium fluoride. Sodium fluoride is particularly preferred. Preferably the instant compositions provide from about 50 ppm to 10,000 ppm, more preferably from about 100 to 3000 ppm, of fluoride ions in the compositions that contact dental surfaces when used with the delivery system of the present invention.

4. Anti-microbial Agents

Anti-microbial agents can also be present in the oral care compositions or substances of the present invention. Such agents may include, but are not limited to, 5-chloro-2-(2,4-dichlorophenoxy)phenol, commonly referred to as triclosan, and described in The Merck Index, 11th ed. (1989), pp. 1529 (entry no. 9573) in U.S. Pat. No. 3,506,720, and in European Pat. Application No. 0,251,591 of Beecham Group, PLC, published Jan. 7, 1988; phthalic acid and its salts including, but not limited to those disclosed in U.S. Pat. No. 4,994,262, Feb. 19, 1991, preferably magnesium monopotassium phthalate, chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zincistannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

5. Anti-inflammatory Agents

Anti-inflammatory agents can also be present in the oral care compositions or substances of the present invention. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx an effective amount of an NSAID.

6. Nutrients

Nutrients may improve the condition of the oral cavity and can be included in the oral care compositions or substances of the present invention. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., © 1997, pp. 10–17.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., ©1997, pp. 3–10.

Oral nutritional supplements include amino acids, lipotropics, fish oil, and mixtures thereof, as disclosed in Drug Facts and Comparisons (loose leaf drug information service), Wolters Kluer Company, St. Louis, Mo., ©1997, pp. 54–54e. Amino acids include, but, are not limited to L-Tryptophan, L-Lysine, Methionine, Threonine, Levocamitine or L- carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, com oil, safflower oil, medium chain triglycerides as disclosed in Drug Facts and Comparisons (loose leaf drug information service), Wolters Kluer Company, St. Louis, Mo., ©1997, pp. 55–57.

7. Mouth and Throat Products

Other materials that can be used with the present invention include commonly known mouth and throat products. Such products are disclosed in Drug Facts and Comparisons (loose leaf drug information service), Wolters Kluer Company, St. Louis, Mo., ©1997, pp. 520b–527. These products include, but, are not limited to anti-fungal, antibiotic and analgesic agents.

8. Antioxidants

Antioxidants are generally recognized as useful in compositions such as those of the present invention. Antioxidants are disclosed in texts such as Cadenas and Packer, The Handbook of Antioxidants, ©1996 by Marcel Dekker. Inc. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

9. H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been denned as H-1 receptors (Ash, A.S.F. & H.O. Schild, Brit. J. Pharmacol Chemother., Vol. 27 (1966), p. 427. Histamine also stimulates the secretion of acid by the stomach (Loew, E.R. & O. Chickering, Proc. Soc. Exp. Biol. Med., Vol. 48 (1941), p. 65), increases the heart rate (Trendelenburg, U., J. Pharmacol., Vol. 130 (1960), p. 450), and inhibits contractions in the rat uterus (Dews, P. B. & J. D. P. Graham, Brit. J. Pharmacol. Chemother., Vol. 1 (1946), p. 278); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine- sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine H2-Receptors", Nature, Vol. 236 (Apr. 21, 1972), pp. 385–390 (Black), as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-52368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408. 4. Particularly preferred is cimetidine (SKF-92334), N-cyano-N'-methyl-N"-(2-(((5-methyl-1H-imidazol-4-yl)methyl)thio)ethyl)guanidine:

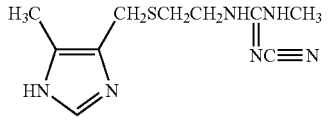

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

10. Analgesic Actives

Anti-pain or desensitizing agents can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc.

11. Anti-viral Actives

Antiviral actives useful in the present composition include any know actives that are routinely use to treat viral infections. Such anti-viral actives are disclosed in Drug Facts and Comparisons (loose leaf drug information service), Wolters Kluer Company, St. Louis, Mo., ©1997, pp. 402(a)–407(z), incorporated herein by reference in its entirety. Specific examples include anti-viral actives disclosed in U.S. Pat. No. 5,747,070, issued May 5, 1998 to Satyanarayana Majeti, incorporated herein by reference in its entirety. Said Patent discloses the use of stannous salts to control viruses. Stannous salts and other anti-viral actives are described in detail in Kirk & Othmer, Encyclopedia of Chemical Technology, Third Edition, Volume 23, Wiley-Interscience Publishers (1982), pp. 42–71, incorporated herein by reference in its entirety. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

12. Other Ingredients

In addition to the above materials of the composition of the present invention, a number of other components may desirably be added to the oral care substance. Additional components include, but are not limited to, flavoring agents, sweetening agents, xylitol, opacifiers, coloring agents, surfactants, and chelants such as ethylenediaminetetraacetic acid. Suitable flavoring agents include, but are not limited to, oil of peppermint, oil of sassafras, clove bud oil, peppermint, menthol, anethole, thymol, methyl salicylate, eucalyptol, cassia, 1-menthyl acetate, sage, eugenol, parsley oil, oxanone, oil of wintergreen, alpha-irisone, oil of spearmint, marjoram, lemon, orange, banana, propenyl guaethol, innamon, and mixtures thereof.

Pigments may also added to the compositions herein to more precisely indicate the locations at which the composition has actually been applied, allowing the user to apply the composition more thoroughly or evenly. However, such pigments are not intended to mask stains that may exist on the tooth surfaces.

These additional ingredients can also be used in place of the compounds disclosed above.

Release Liner

The optional release liner may be formed from any material which exhibits less affinity for the oral care substance than the oral care substance exhibits for itself and for the backing strip. The release liner preferably comprises a rigid sheet of material such as polyethylene, paper, polyester, or other material which is then coated with a non-stick type material. The release liner material may be coated with wax, silicone, teflon, fluoropolymers, or other non-stick type materials. A preferred release liner is Scotchpak®, produced by 3M. The release liner may be cut to substantially the same size and shape as the backing strip or the release liner may be cut larger than the backing strip to provide a readily accessible means for separating the material from the backing strip. The release liner may be formed from a brittle material which cracks when the backing strip is flexed or from multiple pieces of material or a scored piece of material. Alternatively, the release liner may be in two overlapping pieces such as a typical adhesive strip bandage design. A further description of materials suitable as release agents is found in Kirk-Othmer Encyclopedia of Chemical Technology, Fourth Edition, Volume 21, pp. 207–218, incorporated herein by reference.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

One example of a preferred backing strip is a 0.013 mm thick piece of polyethylene film. The backing strip may be provided with an array of shallow pockets, typically 0.4 mm across and 0.1 mm deep. The backing strip has a flexural stiffness of about 0.6 grams/centimeter as measured on a Handle-O-Meter, model #211–300, available from Thwing-Albert Instrument Co. of Philadelphia, Pa., as per test method ASTM D2923-95.

Another example of a preferred backing strip is a 0.3 mm thick piece of substantially water soluble material such as rice paper. Another example of a preferred backing strip is a 0.3 mm thick piece of pullulan paper.

Any of the oral care compositions described below can be used with any of the backing strips described herein.

TABLE 1

Hydrophobic Oral Care Composition

| Component | Ex. 1 | Ex. 2 | Ex. 3 | Ex. 4 | Ex. 5 | Ex. 6 |
|---|---|---|---|---|---|---|
| Organosiloxane Resin[1] | 25 | 25 | 24.6 | 25 | 25 | 25 |
| Silicone Gum[2] | 12.5 | 4.2 | 3.5 | 2.5 | 1.8 | — |
| Oral Care Substance[3] | 17 | 17 | 17 | 17 | 17 | 17 |
| Carrier[4] | 44.5 | 52.8 | 53.9 | 54.5 | 55.2 | 57.0 |
| Bentone Clay[5] | 1 | 1 | 1 | 1 | 1 | 1 |
| | 100 | 100 | 100 | 100 | 100 | 100 |

[1]E.g., MQ resin available as 1170-002 from General Electric.
[2]E.g., Dimethicone gum available as SE 30 or SE 63 from General Electric.
[3]E.g., Sodium percarbonate as a dry powder.
[4]E.g., Isododecane or a 50/50 mixture of ethyl acetate and butanone or a mixture of ethyl acetate, propyl acetate and HFE. The percentage of each individual solvent component in the mixed solvent systems can vary from 0 to 100%, respectively.
[5]Bentone 27 available from Rheox.

TABLE 2

Hydrophobic Oral Care Composition

| Component | Ex. 1 | Ex. 2 | Ex. 3 | Ex. 4 |
|---|---|---|---|---|
| Organosiloxane Resin[1] | 33.43 | 33.43 | 35.14 | 33.43 |
| Silicone Gum[2] | 5.57 | 5.57 | 5.86 | 5.57 |
| Oral Care Substance[3] | 19.00 | 12.00 | 19.00 | 19.00 |
| Ethyl acetate | 8.00 | 8.50 | 8.00 | 8.00 |
| Bentone Gel[4] | 10.00 | 10.00 | 10.00 | 10.00 |
| DC-200/350 cst[5] | 1.00 | 1.00 | 2.00 | 1.00 |
| HFE-7100[6] | 21.00 | 26.00 | — | 19.50 |
| N-propyl acetate | 2.00 | 2.00 | — | 2.00 |
| 2-butanone | — | — | 19.00 | — |
| Aerosil 200[7] ($SiO_2$) | — | — | 1.00 | — |
| Flavor | — | 1.50 | — | 1.50 |
| TOTAL | 100 | 100 | 100 | 100 |

[1]E.g., MQ resin available as 1170-002 from General Electric.
[2]E.g., Dimethicone gum available as SE 30 from General Electric.
[3]E.g., Sodium percarbonate as a dry powder.
[4]Bentone Gel IPM available from Rheox.
[5]DC-200/350 is: dimethylpolysiloxane, CAS# 9016-00-6, from Dow Corning.
[6]HFE-7100 is a mixture of Methyl Nonafluoroisobutyl Ether, CAS# 163702-08-7 and Methyl Nonafluorobutyl Ether, CAS# 163702-07-6 manufactured by 3M Co.
[7]Aerosil 200 is silicon dioxide (chemically prepared), CAS# 112945-52-5, from Degussa AG.

Method of Preparation of Oral Care Composition

The compositions of Tables 1 and 2 are non-aqueous. The oral care substances are dispersed or dissolved in a solution comprising the organosiloxane resin, the fluid diorganopolysiloxane polymer, the carrier, and the rheology modifier.

The hydrophobic compositions of Tables 1 and 2 are suitably prepared as follows. Three hundred (300) grams of organosiloxane resin solution (for example, 43.7% MQ resin in isododecane, or in a 50/50 mixture of ethyl acetate and butanone, or in a mixture of ethyl acetate, propyl acetate and HFE) are mixed with 147.30 grams of fluid diorganopolysiloxane polymer solution (for example, 50% SE30 silicone gum in isododecane or, a 50/50 mixture of ethyl acetate and butanone, or a mixture of ethyl acetate, propyl acetate, and HFE.). The oral care substances are then dispersed in the resin/gum mixture. This method may be carried out without the presence of the silicone gum.

All oral care substances described herein can formulated as described above.

TABLE 3

| Whitening Compositions | | | |
|---|---|---|---|
| Component | Ex. 1 | Ex. 2 | Ex. 3 |
| Organosiloxane Resin[1] | 48.00 | 48.00 | 36.00 |
| Silicone Gum[2] | 8.00 | 6.86 | 9.00 |
| Oral Care Substance[3] | 19.00 | 12.00 | 19.00 |
| Rheology Modifier[4] | 13.00 | 15.00 | 10.00 |
| DC-200/350 cst[5] | 5.00 | 10.00 | 25.00 |
| Surfactant[6] | 6.00 | 8.14 | — |
| Flavor | 1.00 | — | 1.00 |

[1]E.g., MQ resin available as 1170-002 from General Electric.
[2]E.g., Dimethicone gum available as SE 30 from General Electric.
[3]E.g., Sodium percarbonate as a dry powder.
[4]Bentone Gel IPM available from Rheox.
[5]DC-200/350 is: dimethylpolysiloxane, CAS# 9016-00-6, from Dow Corning.
[6]Can be anionic, cationic, or neutral

Method of Preparation

The compositions of Table 3 may be prepared as above, except that a carrier is not added, and the surfactant and flavorant are added after the resin and silicone gum have been mixed until completely dissolved.

All oral care substances described herein can formulated as described above.

TABLE 4

| Whitening Compositions | | | | | | |
|---|---|---|---|---|---|---|
| Component | Ex. 1 | Ex. 2 | Ex. 3 | Ex. 4 | Ex. 5 | Ex. 6 |
| Ethyl Acetate | 18.00 | 14.85 | 22.25 | 20.88 | 18.96 | 18.00 |
| 2-Butanone | 18.00 | 13.00 | 13.10 | 20.88 | 10.00 | 18.00 |
| Isododecane | — | 10.00 | — | — | 11.54 | — |
| Limonene | — | 4.35 | — | — | 5.00 | — |
| MQ Resin | 28.00 | 32.50 | 26.50 | 27.33 | 36.00 | 31.50 |
| SE 30 Silicon Gum | 7.00 | — | 8.80 | 13.67 | — | — |
| Silicone Visc-100M | — | — | — | — | — | 3.50 |
| Silicone Fluid 10 cStk | — | 6.50 | — | — | 9.00 | — |
| Bentone Gel ISD | 10.00 | — | 6.40 | 9.95 | — | 10.00 |
| Claytone HY | — | 2.45 | — | — | 3.00 | — |
| Cab-o-Sil | — | — | 1.50 | — | — | — |
| Sodium Percarbonate | 19.00 | — | 19.00 | 7.00 | — | 19.00 |
| Carbamide Peroxide | — | 15.00 | — | — | 5.00 | — |
| Bismuth Oxychloride | — | 1.15 | — | — | — | — |
| Titanium Dioxide | — | — | 1.00 | — | 1.50 | — |
| Flavor Oil | — | — | 0.15 | — | — | — |
| Sodium Fluoride | — | — | 1.00 | — | — | — |
| Sodium Saccharin | — | 0.20 | 0.30 | 0.30 | — | — |
| | 100.00 | 100.00 | 100.00 | 100.00 | 100.00 | 100.00 |

TABLE 5

| Oral Care Compositions | | | | | |
|---|---|---|---|---|---|
| Component | Ex. 1 | Ex. 2 | Ex. 3 | Ex. 4 | Ex. 5 |
| Ethyl Acetate | 24.50 | 27.75 | 22.00 | 19.96 | 21.10 |
| 2-Butanone | 24.50 | 16.30 | 22.00 | 10.00 | 21.10 |
| Isododecane | — | — | — | 11.54 | — |

TABLE 5-continued

| Oral Care Compositions | | | | | |
|---|---|---|---|---|---|
| Component | Ex. 1 | Ex. 2 | Ex. 3 | Ex. 4 | Ex. 5 |
| Limonene | — | — | — | 5.00 | — |
| MQ Resin | 30.40 | 33.00 | 28.80 | 36.00 | 32.84 |
| SE 30 Silicon Gum | 7.60 | 11.00 | 14.40 | — | 8.21 |
| Silicone Fluid 10 cStk | — | — | — | 9.00 | — |
| Bentone Gel ISD | 10.00 | 8.00 | 10.50 | — | 11.75 |
| Claytone HY | — | — | — | 3.00 | — |
| Cab-o-Sil | — | 1.50 | — | — | — |
| Bismuth Oxychloride | — | 1.00 | — | — | — |
| Titanium Dioxide | — | — | — | 2.00 | — |
| Flavor Oil | — | 0.15 | — | — | — |
| Potassium Nitrate | — | — | — | — | 5.00 |
| Sodium Chlorite | 3.00 | — | — | — | — |
| Tripolyphosphate | — | — | — | 2.50 | — |
| Sodium Fluoride | — | 1.00 | — | 1.00 | — |
| Chlorhexidine Gluconate | — | — | 2.00 | — | — |
| Sodium Saccharin | — | 0.30 | 0.30 | — | — |
| | 100.00 | 100.00 | 100.00 | 100.00 | 100.00 |

TABLE 6

| Oral Care Compositions | | | | | | |
|---|---|---|---|---|---|---|
| Component | Ex. 1 | Ex. 2 | Ex. 3 | Ex. 4 | Ex. 5 | Ex. 6 |
| Ethyl Acetate | 26.00 | 22.00 | 35.00 | 28.00 | 25.77 | 23.00 |
| 2-Butanone | 25.95 | 17.00 | 9.00 | 14.50 | 25.50 | 23.45 |
| Isododecane | — | 10.00 | — | — | 5.00 | — |
| Limonene | — | 4.00 | — | — | — | — |
| MQ Resin | 28.00 | 32.50 | 33.00 | 35.00 | 27.00 | 28.00 |
| SE 30 Silicon Gum | 7.00 | — | 11.00 | 5.00 | 3.00 | 7.00 |
| Silicone Fluid 10 cStk | — | 6.50 | — | — | — | — |
| Bentone Gel ISD | 10.00 | — | 8.00 | 10.00 | 10.00 | — |
| Claytone HY | — | 2.00 | — | — | — | 7.00 |
| Cab-o-Sil M7D | — | — | 1.50 | — | — | — |
| Bismuth Oxychloride | — | 5.00 | — | — | — | 10.00 |
| Titanium Dioxide | 3.00 | — | 1.00 | 5.00 | 2.00 | — |
| Flavor Oil | — | — | 0.10 | — | 0.15 | 0.15 |
| Polymethylsil-sesquioxane | — | — | 1.00 | — | — | — |
| Polymethyl-methyacrylate | 3.00 | 1.00 | — | — | 0.50 | — |
| Nylon 12 | — | — | — | 2.00 | — | 1.00 |
| Silica | — | — | — | — | 0.50 | — |
| FD&C Yellow #5 Al Lake | 0.05 | — | 0.10 | — | 0.05 | 0.10 |
| Iron Oxide, Red | — | — | — | 0.50 | 0.03 | — |
| Sodium Saccharin | — | — | 0.30 | 13 | 0.50 | 0.30 |
| | 100.00 | 100.00 | 100.00 | 100.00 | 100.00 | 100.00 |

TABLE 7

| Ethanol Based Compositions | | | | | | |
|---|---|---|---|---|---|---|
| Component | Ex. 1 | Ex. 2 | Ex. 3 | Ex. 4 | Ex. 5 | Ex. 6 |
| Ethanol | 20.90 | 35.80 | 41.70 | 25.89 | 23.10 | 23.55 |
| Ethyl Acetate | — | — | — | — | 4.95 | — |
| Ethyl Butyrate | 10.30 | — | — | 12.74 | 11.75 | 10.9 |
| Isoamyl Acetate | — | — | — | — | — | 2.65 |

TABLE 7-continued

| Ethanol Based Compositions | | | | | | |
|---|---|---|---|---|---|---|
| Component | Ex. 1 | Ex. 2 | Ex. 3 | Ex. 4 | Ex. 5 | Ex. 6 |
| Isododecane | — | 13.00 | — | — | — | — |
| MQ Resin | 35.10 | 32.85 | 42.75 | 47.00 | 42.00 | 41.80 |
| Silicone Visc-100M | — | — | — | — | 7.15 | — |
| Silicone Fluid 100 cSt | 7.80 | — | — | 9.65 | — | 8.55 |
| Silicone Fluid 10 cStk | 3.90 | — | 11.40 | — | 4.00 | — |
| Silwet L-7500 | — | — | — | — | — | 6.58 |
| Bentone 27 | 1.50 | — | 2.00 | 1.85 | 1.35 | 1.97 |
| Claytone APA | — | 2.00 | — | — | — | — |
| Cab-o-Sil | — | — | — | — | 0.45 | — |
| Sodium Percarbonate | 19.00 | — | — | — | — | — |
| Carbamide Peroxide | — | 15.00 | — | — | — | — |
| Potassium Nitrate | — | — | — | — | 5.00 | — |
| Tripoly-phosphate | — | — | — | — | — | 2.50 |
| Chlorhexidine Digluconate | — | — | — | 2.57 | — | — |
| Titanium Dioxide | 1.50 | — | 2.00 | — | — | 1.50 |
| Flavor Oil | — | — | 0.05 | — | — | — |
| Sodium Fluoride | — | — | 0.10 | — | 0.25 | — |
| Sodium Saccharin | — | 0.20 | 13 | 0.30 | — | — |
| | 100.00 | 100.00 | 100.00 | 100.00 | 100.00 | 100.00 |

Method of Preparation of Composition

The compositions of Tables 4–7 are suitably prepared as follows. Add the solvents into a container suitable to minimize solvent loss. Add the rheology modifiers and mix until well dispersed. Add the silicone resin and mix until completely dissolved. Add the silicone gum and/or silicone fluids and mix until completely dissolved. At this time add any salts such as sodium percarbonate and/or other oral care actives, aesthetic ingredients such as opacifiers, sweeteners, dyes, and flavors. Continue mixing until homogeneous. Additional high shear mixing may be used to promote the mixing. Pack into airtight containers.

Alternatively premixes of the silicone resin and/or the silicone gum may be prepared prior to incorporation into the final blending step to facilitate silicone dissolution and ease of manufacturing. Depending on the formula composition, the order of ingredient addition may also vary such as the addition of the rheology modifier(s) may be moved to a later step allowing lower viscosity to be maintained until the later stages of the blending step.

Method of Preparation of Backing Strip Plus Oral Care Composition

After making the composition according to the any of the methods described above, cast the composition onto a piece of backing strip material (rice paper, for example). Then dry it for about 10–60 minutes to allow some of the volatile component of the carrier, if present, to volatize. A adhesive film will form on the backing strip material. The thickness of adhesive film can be controlled by the amount of the composition used when the composition is cast onto the backing strip. Then cut the backing strip into the desired shape and size.

Methods of Use

In practicing the present invention, a backing strip is applied to the desired oral surface by the wearer. The side of the strip facing the oral surface is coated with an oral care composition that is preferably in a highly viscous state.

The backing strip readily conforms to the oral care surface during application by lightly pressing it there against. The backing strip can be left in oral cavity if it is substantially water soluble or can be peeled off if it is substantially water insoluble. After the strip has dissolved in-situ or has been peeled away by the user, the oral care composition remains on the oral surfaces as a thin a film.

In practicing the present invention, the user need only apply a backing strip that has been coated with composition herein that contains the oral care substance or substances necessary in order to obtain a desired effect, e.g., whitening, breath freshening, caries prevention, pain relief, gum health, tartar control, etc. to the tooth surfaces in the areas desired. The compositions may also be applied to other surfaces of the oral cavity, such as the gingival or mucosal tissues, or to any other oral cavity surface.

Prolonged delivery of the oral care substance is made possible as the oral care substance is released from the film over time. Then, any residual oral care substance may be easily removed by wiping, brushing or rinsing the oral surface after a desired period of time has elapsed, or in the normal course of tooth brushing or other oral care activities. Without being bound by theory, it is believed that the film will last from about 2 hours to 8 hours regardless of the reactivity of the oral care substance. Preferably, the compositions are almost unnoticeable when applied to the oral cavity.

It is not necessary to prepare the oral cavity before using the system of the present invention. For example, the user may or may not choose to brush the teeth or rinse the mouth before using the system. The surfaces of the oral cavity are neither required to be rigorously dried nor to be excessively wet with saliva or water before the system is used. However, it is believed that adhesion to the tooth enamel surfaces will be improved if the teeth are dry when the system is applied.

It should be understood that the present invention relates not only to methods for delivering an oral care substance to the oral cavity of a human, but also to methods of delivering an oral care substance to the oral cavity of an animal, e.g., household pets or other domestic animals, or animals kept in captivity.

It is understood that the examples and embodiments described herein are for illustrative purposes only and that various modifications or changes in light thereof will be suggested to one skilled in the art without departing from the scope of the present invention.

What is claimed is:

1. A delivery system for delivering an oral care substance to the oral cavity, the delivery system comprising:

(a) a removable backing strip having sufficient flexibility so as to be readily conformable to an oral surface when the delivery system is placed thereagainst; and (b) an oral care composition *that forms a film when* applied to the backing strip such that when the delivery system is placed on the oral surface the oral care composition contacts the oral surface, the oral care composition comprising:

(i) an organosiloxane resin;

(ii) a rheology modifier; and (iii) at least one oral care substance;

wherein the oral care composition remains on the oral surface after the backing strip is removed.

2. The delivery system of claim 1 wherein the organosiloxane resin is present in the composition at a level of from about 5% to about 70%.

3. The delivery system of claim 2 wherein the organosiloxane resin is selected from the group consisting of $(CH_3)_3SiO)_{0.5}$ "M" units, $(CH_3)_2SiO$ "D" units, $(CH_3)SiO_{1.5}$ "T" units, $SiO_2$ "Q" units, and mixtures thereof.

4. The delivery system of claim 1 wherein the oral care substance includes at least one oral care active selected from the group consisting of a teeth whitening active, an anti-tartar agent, a fluoride ion source, an anti-microbial agent, an anti-inflammatory agent, one or more nutrients, [a mouth and throat product,] *an anti-fungal, an antibiotic,* an antioxidant, an H2 antagonist, an analgesic active, an anti-viral agent, flavoring agents, sweetening agents, xylitol, opacifiers, coloring agents, surfactants, chelants, pigments, and mixtures thereof.

5. The delivery system of claim 4 wherein the oral care substance comprises from about 0.01% to about 50% of the oral care composition.

6. The delivery system of claim 5 wherein the oral care substance is a teeth whitening active selected from the group consisting peroxides, metal chlorites, perborates, percarbonates, peroxyacids, persulfates, and mixtures thereof.

7. The delivery system of claim 1 wherein the rheology modifier is selected from the group consisting of organo modified clays, silicas, polyethylene, and mixtures thereof.

8. The delivery system of claim 7 wherein the rheology modifier is present in the oral care composition at a level of from about 0.1% to about 30%.

9. A delivery system for delivering an oral care substance to the oral cavity, the delivery system comprising:

(a) a removable backing strip having sufficient flexibility so as to be readily conformable to an oral surface when the delivery system is placed thereagainst; and (b) an oral care composition applied to the backing strip such that when the delivery system is placed on the oral surface the oral care composition contacts the oral surface, the oral care composition comprising:

(i) an organosiloxane resin;

(ii) a fluid diorganopolysiloxane-based polymer;

(iii) a rheology modifier; and (iv) at least one oral care substance;

wherein the oral care composition remains on the oral surface after the backing strip is removed.

10. The delivery system of claim 9 wherein the oral care composition further comprises a carrier capable of solubilizing the organosiloxane resin and the fluid diorganopolysiloxane-based polymer.

11. The delivery system of claim 10 wherein the fluid diorganopolysiloxane-based polymer comprises repeating units of the formula $(R_2SiO)_n$, where R is a monovalent hydrocarbon radical group containing from 1 to 6 carbon atoms.

12. The delivery system of claim [1] *9* wherein the fluid diorganopolysiloxane polymer is poly(dimethylsiloxane).

13. The delivery system of claim 9 wherein the ratio of organosiloxane resin to fluid diorganopolysiloxane-based polymer is from about 10:1 to about 1:10.

14. The delivery system of claim 10 wherein the carrier is selected from the group consisting of hydrocarbon oils, volatile silicones, non-hydrocarbon solvents, and-mixtures thereof.

15. The delivery system of claim 9 wherein the oral care substance includes at least one oral care active selected from the group consisting of a teeth whitening active, an anti-tartar agent, a fluoride ion source, an anti-microbial agent, an anti-inflammatory agent, one or more nutrients, [a mouth and throat product,] *an anti-fungal, an antibiotic,* an antioxidant, an H2 antagonist, an analgesic active, an anti-viral agent, flavoring agents, sweetening agents, xylitol, opacifiers, coloring agents, surfactants, chelants, pigments, and mixtures thereof.

16. The delivery system of claim 15 wherein the oral care active comprises from about 0.01% to about 50% of the oral care composition.

17. The delivery system of claim 16 wherein the oral care active is a teeth whitening active selected from the group consisting peroxides, metal chlorites, perborates, percarbonates, peroxyacids, persulfates, and mixtures thereof.

18. The delivery system of claim 9 wherein the rheology modifier is selected from the group consisting of organo modified clays, silicas, polyethylene, and mixtures thereof.

19. The delivery system of claim 9 wherein the rheology modifier is present in the oral care composition at a level of from about 0.1% to about 30%.

20. The delivery system of either of claim 1 or claim 9 wherein the backing strip is substantially water insoluble.

21. The delivery system of claim 20 wherein the backing strip is a polymer film having a [nominal] thickness of less than about 0.1 mm and selected from the group consisting of polyethylene, ethylvinylacetate, polyesters, ethylvinyl alcohol, pullulan film, and combinations thereof.

22. The delivery system of claim 21 wherein the backing strip has a peel force, of less than 50 grams.

23. The delivery system of either of claim 1 or claim 9 wherein the backing strip is substantially water soluble.

24. The delivery system of claim 23 wherein the backing strip is selected from the group consisting of rice paper, pullulan paper, agar film, starch paper, *a* natural gum, and mixtures thereof.

25. A method for delivering an oral care substance to at least one surface of the oral cavity, comprising the steps of: (1) applying the backing strip of the delivery system with the oral care composition of either of claim 1 or claim 9 coated thereon to the surface(s) of the oral cavity; (2) removing the backing strip from the surface(s) of the oral cavity, wherein the oral care composition remains on the surface(s) of the oral cavity after the backing strip is removed.

26. The method of claim 25 wherein the oral care composition comprises a teeth whitening active and the oral cavity surface to which the composition is applied is the enamel of the teeth.

27. A method for delivering an oral care substance to at least one surface of the oral cavity, comprising the steps of: (1) applying the backing stip of the delivery system with the oral care composition of either of claim 1 or claim 9 coated thereon to the surface(s) of the oral cavity; (2) allowing the backing strip to dissolve in situ, wherein the oral care composition remains on the surface(s) of the oral cavity after the backing strip has dissolved.

28. The method of claim 27 wherein the oral care composition comprises a teeth whitening active and the oral cavity surface to which the composition is applied is the enamel of the teeth.

*29. A tooth whitening system, comprising:*

*a backing material comprising a water soluble material that dissolves during use; and*

*a tooth whitening composition comprising an organosiloxane resin applied to one side of said backing material, wherein the system is sized for application to both front and rear surfaces of a plurality of adjacent teeth.*

*30. The tooth whitening system of claim 29, wherein said tooth whitening composition comprises a peroxide.*

*31. The tooth whitening system of claim 30, wherein said peroxide is hydrogen peroxide.*

*32. The tooth whitening system of claim 30, wherein said peroxide has a concentration between about 0.1% and about 20% by weight of the tooth whitening composition.*

*33. The tooth whitening system of claim 29, wherein said water soluble material is selected from the group consisting of agar film, starch paper, rice paper, a natural gum, pullulan paper, and mixtures thereof.*

*34. The tooth whitening system of claim 29, wherein said tooth whitening composition is a laminate.*

*35. The tooth whitening system of claim 29, wherein said backing material is a laminate.*

*36. The tooth whitening system of claim 29, wherein said backing material has a width between about 1.5 cm and about 2 cm.*

*37. The tooth whitening system of claim 29, wherein said water soluble material is substantially water soluble.*

*38. The tooth whitening system of claim 29, wherein the tooth whitening composition forms a film when applied to one side of said backing material.*

*39. The tooth whitening system of claim 29, further comprising a release liner.*

*40. The tooth whitening system of claim 29, further comprising a rheology modifier.*

*41. The tooth whitening system of claim 40, wherein the rheology modifier is selected from the group consisting of: organo modified clays, silicas, polyethylene, and mixtures thereof.*

* * * * *